United States Patent [19]

Nash

[11] Patent Number: 5,779,721
[45] Date of Patent: Jul. 14, 1998

[54] SYSTEM AND METHOD OF USE FOR REVASCULARIZING STENOTIC BYPASS GRAFTS AND OTHER BLOOD VESSELS

[75] Inventor: John E. Nash, Downingtown, Pa.

[73] Assignee: Kensey Nash Corporation, Exton, Pa.

[21] Appl. No.: 690,438

[22] Filed: Jul. 26, 1996

[51] Int. Cl.$^6$ ............................................. A61B 17/22
[52] U.S. Cl. ............................................. 606/159
[58] Field of Search .......................... 606/159, 170, 606/180; 604/22

[56] References Cited

U.S. PATENT DOCUMENTS

| | | |
|---|---|---|
| 4,445,509 | 5/1984 | Auth . |
| 4,589,412 | 5/1986 | Kensey .................... 606/159 |
| 4,631,052 | 12/1986 | Kensey . |
| 4,686,982 | 8/1987 | Nash . |
| 4,700,705 | 10/1987 | Kensey et al. . |
| 4,747,821 | 5/1988 | Kensey et al. . |
| 4,749,376 | 6/1988 | Kensey et al. . |
| 4,790,813 | 12/1988 | Kensey . |
| 5,009,659 | 4/1991 | Hamlin et al. . |
| 5,030,201 | 7/1991 | Palestrant . |
| 5,042,984 | 8/1991 | Kensey et al. . |
| 5,074,841 | 12/1991 | Ademovic et al. . |
| 5,097,849 | 3/1992 | Kensey et al. . |
| 5,195,956 | 3/1993 | Stockmeier .................... 606/159 |
| 5,224,945 | 7/1993 | Pannek, Jr. . |
| 5,282,484 | 2/1994 | Reger . |
| 5,366,463 | 11/1994 | Ryan . |
| 5,368,603 | 11/1994 | Halliburton . |
| 5,370,609 | 12/1994 | Drasler et al. . |
| 5,402,790 | 4/1995 | Jang et al. . |
| 5,423,742 | 6/1995 | Theron . |
| 5,429,136 | 7/1995 | Milo et al. . |
| 5,496,267 | 3/1996 | Drasler et al. . |
| 5,679,558 | 10/1997 | Kensey et al. . |

OTHER PUBLICATIONS

Brochure entitled "Rotablator" by HeartTechnology, Inc., publication date unknown.
Brochure entitled "Extraction Atherectomy, Putting Plaque and Thrombus in Their Proper Place" by International Technologies, Inc., publication date unknown.
Publication by Possis Medical Inc. Innovations for Life entitled "AngioJet Rapid Thrombectomy System", pp. 94 and 95, dated May, 1996.
Brochure entitled "Rheolytic Thrombectomy System Angio-Jet" by Possis Medical Inc. Innovations for Life, publication data unknown.
Brochure entitled "Amplatz Thrombectomy Device, The Clot-Buster" by Microvena Corporation, publication date unknown.

*Primary Examiner*—Michael Buiz
*Assistant Examiner*—Kevin Truong
*Attorney, Agent, or Firm*—Caesar, Rivise, Bernstein, Cohen & Pokotilow, Ltd.

[57] ABSTRACT

A system and method for opening a lumen in an occluded blood vessel, e.g., a coronary bypass graft, of a living being's vascular system. The system comprises an instrument having a working head, e.g., a rotary impacting impeller located within an apertured shroud, and a debris extraction sub-system. The instrument is located within a guide catheter. The working head is arranged to operate on, e.g., impact, the occlusive material in the occluded vessel to open a lumen therein, whereupon some debris may be produced by the operation of the working head on the occlusive material. The debris extraction sub-system introduces an infusate liquid at a first flow rate adjacent the working head, e.g., through a opening in the shroud, and withdraws that liquid and some blood at a second and higher flow rate, e.g., through the guide catheter. This action creates a differential flow adjacent the working head, whereupon debris produced by the operation of the working head is withdrawn in the infusate liquid and blood by the differential flow for collection outside the being's body. The introduction of the infusate liquid establishes an unbalanced flow adjacent the working head to enable the catheter to be steered hydrodynamically.

53 Claims, 3 Drawing Sheets

SYSTEM AND METHOD OF USE FOR REVASCULARIZING STENOTIC BYPASS GRAFTS AND OTHER BLOOD VESSELS

BACKGROUND OF THE INVENTION

Catheter instruments have been suggested or disclosed in the patent literature for effecting non-invasive or minimally invasive revascularization of occluded arteries. For example, in U.S. Pat. No. 4,445,509 there is disclosed a recanalization catheter designed specifically for cutting away hard, abnormal deposits, such as atherosclerotic plaque, from the inside of an artery, while supposedly preserving the soft arterial tissue. That recanalizing catheter includes a sharp-edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon relatively hard deposits are cut away from relatively soft tissue. Suction ports are provided to pull the hard particles produced by the cutting action into the catheter for removal at the proximal end thereof so that such particles do not flow distally of the catheter where they could have an adverse effect on the patients' body.

In U.S. Pat. No. 4,700,705, which is assigned to the same assignee as this invention and whose disclosure is incorporated by reference herein, there are disclosed and claimed catheters and methods of use for effecting the opening of a vessel, duct or lumen, such as the opening of a atherosclerotic restriction (partial or total occlusion) in an artery. These catheters are elongated flexible members of sufficient flexibility to enable them to be readily passed through the body of the patient to the situs of the atherosclerotic plaque in the artery to be opened. A working head is mounted at the distal end of the catheter and is arranged for high-speed rotation about the longitudinal axis of the catheter. In some embodiments the catheter may eject fluid at the working head to expedite the restriction-opening procedure.

In U.S. Pat. No. 4,747,821, which is also assigned to the same assignee as this invention and whose disclosure is incorporated by reference herein, there is disclosed and claimed other catheters particularly suited for revascularization of arteries. Each of those catheters includes a rotary working head having at least one non-sharp impacting surface to effect material removal without cutting. Moreover, those catheters are arranged to eject fluid adjacent the working head to expedite the revascularization procedure. In particular, the rotation of the working head produces a powerful, toroidal shaped vortex contiguous with the working head which has the effect of recirculating any particles that may have been broken off from the material forming the arterial restriction so that the working head repeatedly impacts those particles to reduce their size.

In U.S. Pat. No. 5,042,984, which is also assigned to the same assignee as this invention and whose disclosure is incorporated by reference herein, there are disclosed and claimed catheters whose working heads include impacting surfaces of differing aggressiveness which may be selectively brought into engagement with the restriction to be opened. Such catheters also make use of exiting jets of liquid as described above.

Other atherectomy devices for enlarging an opening in a blood vessel have been disclosed and claimed in the following U.S. Pat. Nos.: 4,589,412 (which is assigned to the same assignee as this invention and whose disclosure is incorporated by reference herein); 4,631,052; 4,686,982 (which is assigned to the same assignee as this invention and whose disclosure is incorporated by reference herein); 4,749,376 (which is assigned to the same assignee as this invention and whose disclosure is incorporated by reference herein); 4,790,813; 5,009,659; 5,074,841; 5,282,484; 5,366,463; 5,368,603; 5,402,790; 5,423,742; and 5,429,136.

Some rotary atherectomy devices are in use in this country for revascularizing occluded arteries. However, their use is limited to some very selected applications. Thus, in many instances a vascular occlusion of a coronary artery can only be treated by coronary bypass surgery wherein a graft, e.g., a saphenous vein section and/or mammary artery section, is surgically shunted across the occluded coronary artery. Unfortunately a significant percentage of bypass surgical grafts become re-occluded over time. Thus, the re-occluded graft has to be either bypassed by another graft (i.e., second bypass surgery), or the re-occluded graft has to be revascularized (i.e., its lumen reopened) by some intravascular procedure. If the occluded graft is not totally occluded, balloon angioplasty may be indicated to reopen the graft. Where, however, the graft is totally occluded balloon angioplasty in unavailable. Thus, if revascularization of that graft is desired, resort may be to rotary atherectomy.

One currently available rotary atherectomy device is the ROTOBLACOR® System of Heart Technology, Inc. That system utilizes a catheter having a diamond coated elliptical burr which is rotated at a high rate of speed, e.g., up to 190,000 rpm. The burr serves to break the atherosclerotic plaque into fine particles which are allowed to remain in the patient's body for disposal by the patient's reticuloendothelial system.

As is known to those skilled in the art, one problem with a rotary atherectomy device is that unless the debris produced is so small and benign that it can be left within the patient's vascular system there must be some means to ensure that the debris does not flow upstream into the aorta during the procedure or into the downstream artery graft at the break-through point when the device comes out the distal side of a total occlusion, since either action could present a significant hazard to the patient. In particular, the former route risks stroke, the later route risks local ischemia of heart muscle when debris blocks off small arteries.

Thus, the collection and/or aspiration of debris produced during the revascularization of occluded arterial bypass grafts or other blood vessels is getting considerable attention in the medical arts. For example, Possis Medical, Inc., the assignee of U.S. Pat. Nos. 5,370,609 and 5,496,267, provides catheter devices designated as the ANGIOJET Rapid Thrombolectomy System and the ANGIOJET Rheolytic Thrombolectomy System. These devices are presumably constructed in accordance with those patents and are believed to be presently undergoing clinical trials. The catheter devices disclosed in those patents utilize high velocity jets of saline to abrade the blockage. In particular, the patents disclose utilizing the momentum of the saline jets to create a local vacuum to entrain any particulate material produced by the revascularization procedure, with the momentum and the local positive pressure being sufficient to carry the saline and debris to a return collection bag.

Another atherectomy device which is currently undergoing clinical trials is the Coronary TEC® System of Interventional Technologies, Inc. That device is believed to be the subject of U.S. Pat. No. 5,224,945, and basically comprises a catheter having a working head with microtome sharp blades for cutting plaque circumferentially. The excised plaque is extracted by suction through a central lumen in the catheter into an exteriorly-located vacuum bottle. No control of the quantity of flow of the debris-carrying fluid from the catheter is disclosed.

U.S. Pat. No. 5,030,201 (Palestran) discloses a system including an expandable atherectomy catheter arranged to be rotated to cut through an occluded artery to revascularize it. The atherectomy catheter includes an expandable cutting head having plural elongated cutting members which are mounted on a flexible torque tube incorporating a vacuum or aspiration system for retrieval of excised material. The cutting head is arranged to be rotated to cause the elongated members to cut away atheromatous material or blood clots. The atherectomy catheter is arranged to be inserted into the blood vessel through a coaxial delivery catheter, also forming a part of the system. The mechanism for aspirating particles of atheromatous material or blood clots removed by the elongated cutting members is disclosed as being in the form of a vacuum port provided at the proximal end of either the delivery catheter, the atherectomy catheter or a "retracting catheter" which also constitutes a part of the system. Saline solution or some other irrigant is infused through one of the catheters of the device that is not being used for aspiration. The infusion rate of the saline solution is balanced with the aspiration rate to avoid any net removal of fluid from the vessel. In particular, the patent teaches that by balancing the infusion rate of the saline solution to the aspiration rate, the net removal of fluid from the vessel can be brought close to zero, thereby minimizing blood loss.

While the balancing of the infusion and aspiration flow rates to minimize blood loss may be desirable, such action does not insure positive removal of all debris produced during the revascularization procedure.

Accordingly, a need exists for apparatus and a method of use to revascularize partially or totally occluded blood vessels, while positively assuring that any particles produced during the revascularization procedure are removed from the patient's body. In the case of partially or totally occluded coronary bypass grafts, a need exists for intravascular atherectomy apparatus and methods of use for effectively producing a lumen through the occlusion for the free flow of blood, without the risk that any debris produced during the lumen opening procedure will enter into the aorta or downstream of the occlusion once it has been crossed or opened.

OBJECTS OF THE INVENTION

Accordingly, it is a general object of this invention to provide systems and methods which address those needs.

It is another object of this invention to provide a system and methods for effectively revascularizing partially or totally occluded blood vessels and for removing any debris produced during the procedure from the patient's body.

It is another object of this invention to provide a system and methods for safely revascularizing partially or totally occluded blood vessels.

It is still another object of this invention to provide a system and methods for effectively opening a lumen in a partially or totally occluded arterial bypass graft, without the risk of debris produced during the procedure entering the aorta or from flowing downstream once the lumen through the occlusion has been opened.

It is yet another object of this invention to provide a system and methods for effectively opening a lumen in a partially or totally occluded portion of an artery, e.g., the femoral artery, downstream of a junction with another vessel, e.g., the profunda femoris, without the risk of debris produced during the procedure entering the other vessel or from flowing downstream in the artery once the lumen through the occlusion has been opened.

It is yet a further object of this invention to provide a system and methods for revascularizing partially or totally occluded blood vessels utilizing liquid infusion and aspiration means for establishing a differential flow to positively ensure the aspiration of debris produced during the revascularization procedure.

It is yet a further object of this invention to provide a system and methods for revascularizing partially or totally occluded blood vessels utilizing liquid infusion and aspiration means which is easy to operate to effect the positive removal of debris produced during the revascularization procedure.

It is yet a further object of this invention to provide a system and methods for revascularizing partially or totally occluded blood vessels utilizing liquid infusion and aspiration means which is adjustable for effectuating the positive removal of debris produced during the revascularization procedure.

SUMMARY OF THE INVENTION

These and other objects of this invention are achieved by providing a system for opening a lumen in an occluded blood vessel, e.g., a coronary bypass graft, of a living being's vascular system located downstream of another blood vessel, e.g., the aorta, from which blood will flow to the occluded blood vessel. The system basically comprises a working head for revascularizing the vessel and means for extracting or removing debris produced by operation of the working head.

The working head, e.g., a rotary impacting impeller, is arranged to operate on, e.g., engage, material, such as an atherosclerotic deposit or lesion or thrombus forming the occlusion within the interior of the occluded blood vessel to open a lumen for the flow of blood therethrough.

The debris extraction means is arranged to introduce an infusate liquid at a first flow rate into the vessel adjacent the working head and to withdraw that liquid and some blood at a second and higher flow rate from the vessel. This action creates a differential flow in the vessel, whereupon debris within the vessel which is produced by the action of the working head on the occlusion material is positively withdrawn with the infusate liquid and blood from the vessel for remote collection, e.g., in a collection vessel located outside the body of the person being treated. Thus, the differential flow serves to prevent the debris from flowing into adjacent blood vessels, e.g., the aorta.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED EMBODIMENT

Figure 1:
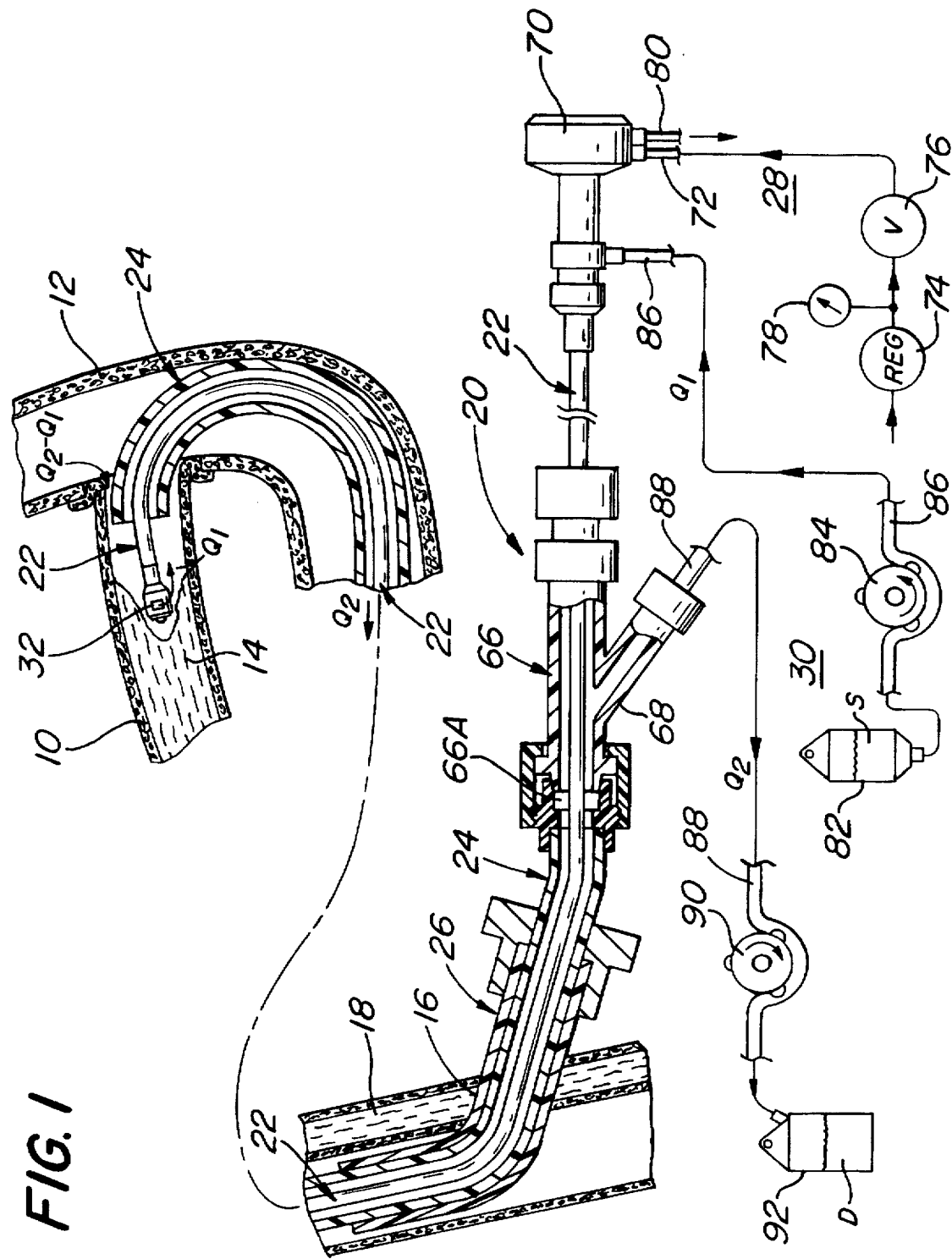
FIG. 1 is a schematic diagram, partially in section, of a system of the subject invention shown during the process of opening a lumen in a totally occluded coronary bypass graft so that blood can flow therethrough.
Figure 2:
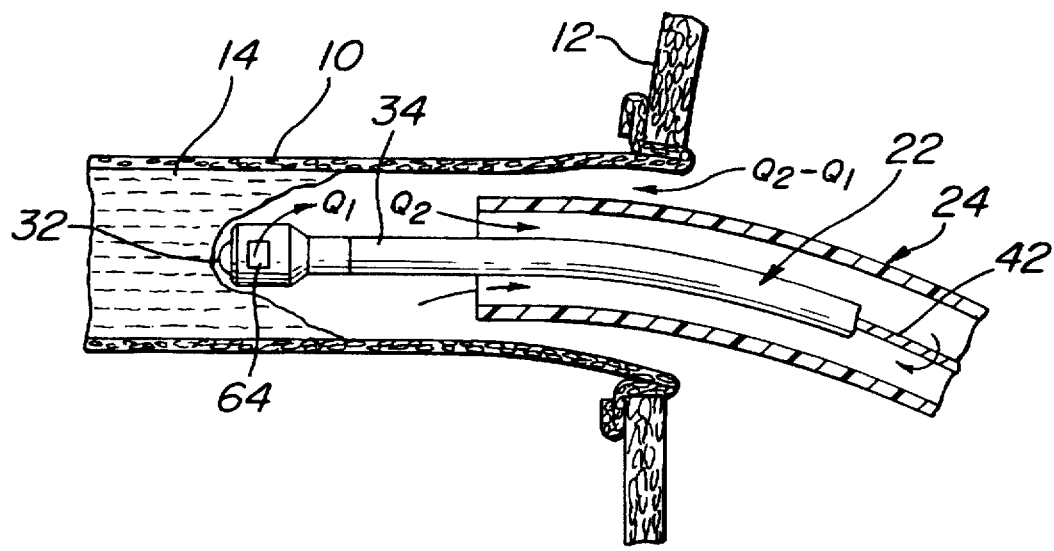
FIG. 2 is an enlarged view, partially in section, of a portion of the system of FIG. 1 shown during the process of opening a lumen in the occluded coronary bypass graft.

Referring now in greater detail to the various figures of the drawings wherein like reference characters refer to like parts, there is shown at 20 in FIG. 1 a system for revascularizing or opening a lumen through a coronary bypass graft which has become occluded, such as by the formation of a stenotic lesion or the build-up of plaque therein. As used herein the term "occluded" is given its broadest interpretation. Thus, an "occluded" graft or blood vessel may be either totally blocked or only partially blocked (i.e., there is a passageway or lumen through which some blood may flow).

The system 20 is arranged to be used for forming or enlarging a lumen through any blood vessel within the body of a living being, e.g., an occluded femoral artery downstream of the profunda femoris, not necessarily an occluded coronary bypass graft or an occluded coronary artery. In particular, the system 20 is arranged to produce a channel or lumen or to enlarge a lumen through the occlusive material with the vessel and to ensure that any particles of that material which are removed or broken away, during the revascularization procedure are prevented from flowing into the contiguous vascular system. When the system 20 is used for revascularization of occluded coronary bypass grafts, a primary application for the system 20, the debris produced is drawn into the system for extracorporeal removal and is thus prevented from entering the aorta.

As can be seen in FIG. 1, the system 20 basically comprises an "atherectomy" catheter 22, a guide catheter 24, an introducer sheath 26, a drive sub-system 28, and a debris removal sub-system 30. The atherectomy catheter 22 is in the form of an elongated flexible tubular body member or jacket at the free or distal end of which is located a rotatable working head 32. The working head 32 is generally similar to that described in U.S. Pat. No. 4,747,821. Alternatively, the working head may be constructed in accordance with the teachings of U.S. Pat. Nos. 4,679,558, 4,686,982, 4,749,376, 5,042,984, and 5,097,849, all of which are also assigned to the same assignee as this invention, and whose disclosures are also incorporated by reference herein. In fact, the working head may be any device for opening a lumen through the occlusive material.

In use the atherectomy catheter 22 is guided through the vascular system of the patient by the guide catheter 24 (which is conventionally placed) to the site of the vascular occlusion that has been determined to exist, so that the rotary working head is located immediately adjacent the upstream end of the occlusion. In the embodiment shown in FIG. 1, the atherectomy catheter is located within a coronary bypass graft 10 having an upstream end in fluid communication with the aorta 12. The downstream end of the graft is not shown and is in fluid communication with the coronary artery being bypassed or with smaller arteries of the heart. In the example shown herein the graft 10 is totally occluded by an atherosclerotic lesion or plaque or some other occlusive material 14 within the interior of the graft.

The atherectomy catheter 22 is introduced into the patient's vascular system in a conventional manner, e.g., via the use of the introducer sheath and guide catheter. As shown, this is accomplished via a percutaneous puncture 16 in the femoral artery 18. The sheath 26 and guide catheter 24 are each of conventional construction and thus their details will not be described in the interest of brevity.

The working head 32 is arranged to rotate about the longitudinal axis of the catheter at a high rate of speed, e.g., from 10,000 rpm to 200,000 rpm to repeatedly mechanically impact the occlusive material. At the same time, an infusate liquid (to be described later) is pumped through the atherectomy catheter by a pump (to be described later and forming a portion of the debris removal sub-system 30) and out of distal end of the atherectomy catheter adjacent the working head.

The opening of the occlusion to allow freer flow of blood therethrough is effected by impacting surfaces of the rotating working head impacting the occlusive material 14, whereupon portions thereof are removed, e.g., broken away. In addition, as will be described later, the rotation of the working head produces a powerful, toroidal shaped vortex contiguous with the working head. This vortex flow has the effect of recirculating any particles that are broken off from the occlusive material by the impact of the rotary working head's impacting surfaces back into contact with such surfaces. Accordingly, those particles are repeatedly impacted over and over, with each impaction reducing the size of the particles further until the resulting particle size is very small, e.g., 95% have a surface area less than that of a red-blood cell. At the same time another pump (also to be described later) of the debris removal sub-system 30 is operated to aspirate the particles produced during the revascularization procedure along with the infusate liquid and some blood.

Thus, as will be described in detail later, the debris removal subsystem 30 is operative to ensure that debris produced as the working head opens a lumen through the occlusion is not able to flow upstream into the upstream vessel, e.g., the aorta 12, during the lumen opening procedure, and once the working head breaks through or exits the occlusion on the downstream side, that the debris is not able to flow downstream into the downstream blood vessel(s).

Figure 4:
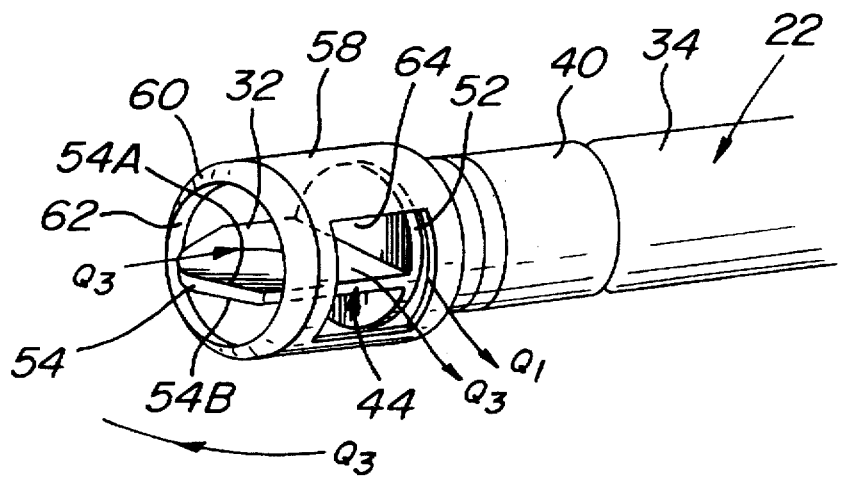
FIG. 4 is a reduced isometric view of the portion of the system shown in FIG. 3.

As best seen in FIG. 4 the atherectomy catheter includes a jacket 34 which is formed of any suitable material, e.g., plastic, and has a small outside diameter. In the preferred embodiment shown herein, the outside diameter of the jacket 34 is approximately 1.5 mm (5 French). This size catheter is merely exemplary. The means for effecting the rotation of the working head is the heretofore identified drive sub-system 28. That subsystem is similar to the drives disclosed in the aforementioned U.S. Pat. Nos. 4,686,982, and 4,747,821 and basically comprises an air-turbine motor and associated rotary drive cable (to be described later). Other drive systems can be utilized, as well.

Irrespective of the construction of the drive system, it is coupled to the working head 32 so that the working head is rotated about its longitudinal axis at the high rate of speed. Many of the details of the working head will be described later. Suffice it for now to say that the working head 32 includes an impeller portion 44 and a central shank portion or axle 36 (FIG. 4) projecting proximally therefrom. The axle 36 is supported in a central bore of a bushing 38 fixedly mounted at the distal end of the catheter's jacket 34 by an encircling mounting band 40. The shank 36 is fixedly secured to the distal end of a flexible drive cable 42 forming a portion of the drive sub-system 28.

The impeller 44 forms the distal portion of the working head and is fixedly secured to the shank 36 so that it will be rotated at a high rate of speed about its longitudinal axis by the concomitant rotation of the drive cable. The impeller portion 44 comprises a circular disk or base 52 from which a generally planar tip 54 projects. The tip 54 has a pair of generally planar diametrically disposed relieved side surfaces or faces which merge with an arcuate front or distal surface to form a pair of arcuate impacting surfaces 54A and 54B. Each of the impacting surfaces is radiused in a plane perpendicular to the axis of rotation of the working head so that each is not sharp, e.g., is in the range of approximately 0.001 inch to approximately 0.008 inch, although in the scale of the figures of the drawing they appear to be a sharp line.

The working head is located within a cylindrical shroud 56 (FIGS. 3 and 4) fixedly mounted on the front of the bushing 38. The shroud 56 includes a cylindrical sidewall portion 58 and a generally conical distal wall portion 60 terminating in a circular opening 62 in the distal end thereof. The shroud may be of any suitable outside diameter, e.g., 7 to 8 French. The distal arcuate portion of the impeller tip 54 projects out of the central or front opening 62. A side port or open window 64 is located in the sidewall 58.

As mentioned earlier the system 20 utilizes an infusate liquid to expedite the revascularization of the vessel. In particular, the infusate liquid is pumped at a flow rate $Q_1$ (to be described later) down through the interior of the catheter jacket 34 through four equidistantly spaced grooves 46 extending down the central bore of the bushing 38 and via radial ports 48 to an annular recess 50 in the front wall of the bushing. The annular recess is in fluid communication with the side port or window 64 in the shroud so that the infusate liquid can exit therefrom. The direction of flow of the infusate liquid down the atherectomy catheter and out the shroud at its working head is shown clearly in FIG. 4.

Figure 3:
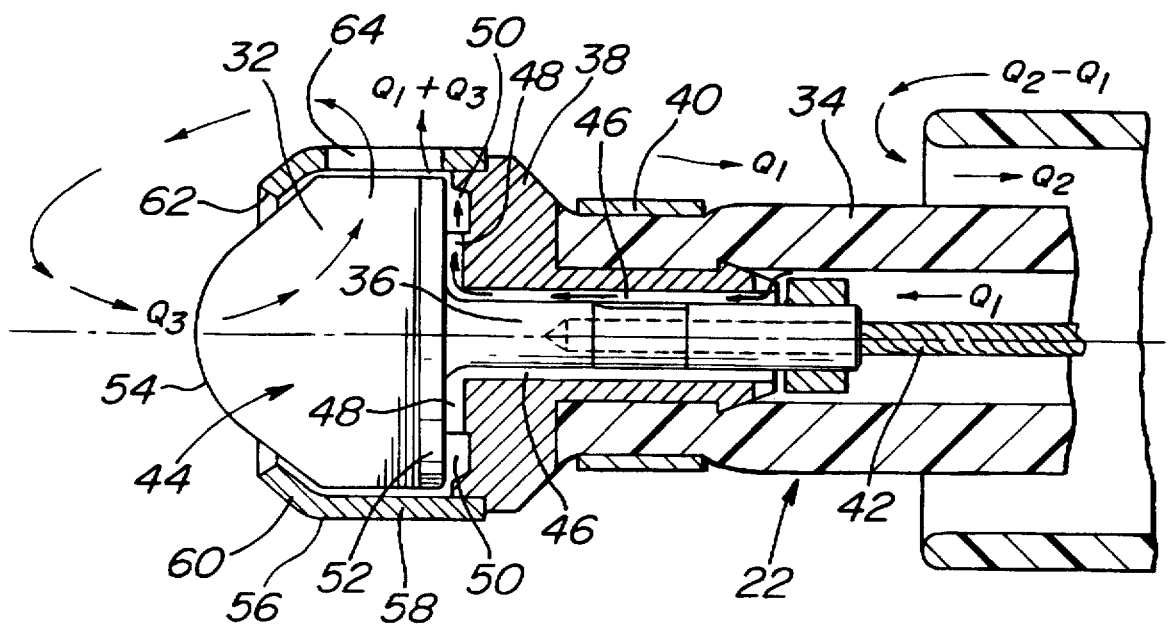
FIG. 3 is an even more greatly enlarged view, partially in section, of a portion of the system shown in FIG. 2.

The rotation of the working head about its longitudinal axis produces a powerful toroidal shaped vortex flow $Q_3$ in the fluid contiguous with the working head. This flow $Q_3$ circulates by entering into the shroud through the central or front opening 62 and exits out through the side window 64 as shown in FIG. 3. Thus, the flow exiting through window 64 is $Q_1+Q_3$. As will be appreciated by those skilled in the art the vortex flow $Q_3$ has the effect of recirculating any particles that are broken off from the occlusive material 14 by the action of the rotating working head back into contact with the working head's impacting surfaces. Thus, the occlusive material particles which are broken away are progressively reduced in size until they are aspirated by aspiration means forming a portion of the debris removal sub-system 30. That means will be described later. Suffice it for now to state that the aspiration means withdraws the infusate liquid, the debris particles and some blood at an aspiration flow rate of $Q_2$.

As should be appreciated by those skilled in the art the liquid exiting from the window 64 of the shroud will tend to push the atherectomy catheter's distal end sideways or laterally in the direction opposite to the direction of the liquid exiting that window. This hydrodynamic action can be effectively used to steer the catheter to a desired position with respect to an occlusion to be revascularized. In this regard, for example, when negotiating a branch in the artery system to reach the occlusion to be revascularized, the atherectomy catheter can be rotated or twisted about its longitudinal axis so that the shroud's window is facing in the opposite direction to the branch to be entered. This action will cause the side directed liquid exiting the window 64 to push the catheter's distal end sideways, whereupon it can enter the desired arterial branch. Such "hydrodynamic steering" of the atherectomy catheter can be accomplished in other manners and by other means than by the use of a shroud having a single side window or port. Thus, this invention contemplates an intravascular catheter instrument, of any type, including any means for producing an asymmetric, e.g., side directed, fluid flow adjacent the distal end of the catheter so that it can be steered into a desired position by appropriate rotation of the catheter about its longitudinal axis.

As mentioned earlier, the guide catheter 24 is of any conventional construction. In the preferred embodiment shown in FIG. 1 it is a 10F to 12F catheter having a conventional Y connector 66 at its proximal end. The Y connector 66 has one input leg including a Touhy-Borst adjustable hemostasis valve 66A through which the atherectomy catheter 22 passes. The other input leg, i.e., the angled leg 68, is connected to the aspiration portion of the debris removal sub-system 30 (to be described later).

Power for operating the atherectomy catheter is provided by the drive sub-system 28. That system includes an air turbine motor 70 which is coupled to the proximal end of the flexible drive cable 42. The air turbine 70 is provided with compressed air via an input line or conduit 72. Air for the line 72 is provided from a source (not shown) via an associated regulator 74, and the conventional control valve 76. The control valve is coupled to the input line 72 of the air turbine. A pressure gauge 78 is connected between the regulator 74 and the control valve 76. The regulator 74, the control valve 76, the pressure gauge 78 and the associated lines or conduits and the air source make up the drive sub-system 28. The control valve 76 is of any conventional construction, be it mechanical or electrical. The air turbine motor 70 is also of any conventional construction, as is the regulator 74 and the pressure gauge 78. The air turbine includes an outlet port in communication with the ambient atmosphere, via a line 80. It must be pointed out at this juncture that the atherectomy catheter 22 need not utilize an air turbine motor to rotate the working head. For example, an electric motor can be provided to replace the air turbine to drive the rotating cable and the associated working head.

The debris removal sub-system 30 basically comprises a source 82 of the infusate liquid "S", e.g., saline plus a 30% contrast media, a first positive displacement pump 84, an input line or conduit 86, an outlet line or conduit 88, a second positive displacement pump 90, and a debris collection vessel 92. The input line 86 and its associated components, i.e., the pump 84 and infusate source 82 serve as the "infusion" means for the system 20. To that end the input line 86 is coupled via a connector to the interior of the atherectomy catheter, i.e., to the annular space within the catheter's jacket between it and the drive cable. The infusate liquid S is pumped at the flow rate $Q_1$ by the positive displacement pump 84 through line 86 from the supply or source 82. Thus, the infusate liquid S exits the catheter's working head and circulates as described earlier.

The rate of flow $Q_1$ of the infusate liquid is established by the positive displacement pump 84 under control of some automatic or manual controller (not shown). In accordance with one exemplary method of use the pump is operated to produce a flow rate $Q_1$ the range of 5–80 ml. per minute.

The output line 88 and its associated components, i.e., the pump 90 and debris collector vessel 92 serve as the "aspirating" means for the debris removal sub-system 30. To that end, the aspiration line 88 is connected to the leg 68 of the Y connector 66. The pump 90 is arranged to be operated to pump the infusate liquid, the debris produced by the revascularization, and some small amount of blood at the flow rate $Q_2$ in the proximal direction through the annular space between the atherectomy catheter 22 and the guide catheter 24 and out through the connector leg 68 into the outlet line 88, and from there to the collector vessel 92.

The flow rate $Q_2$ is selected to be greater than $Q_1$. For example, in one exemplary method of use the flow rate is selected to be in the range of 5-100 ml. per minute, with the differential between $Q_2$ and $Q_1$ being between 5 and 50 percent. The use of an aspiration flow rate $Q_2$ which is higher than the infusion flow rate $Q_1$ insures that any debris, e.g., particles of the occlusive material making up the graft's lesion, produced from debriding that material is positively prevented from flowing into adjacent vessel portions. In this regard, as will be appreciated by those skilled in the art, since the aspiration flow rate $Q_2$ is greater than the infusion flow rate $Q_1$, some blood equal to $Q_2-Q_1$ will also be withdrawn from the upstream vessel, e.g., the aorta as shown in FIGS. 1 and 3. The withdrawal of some blood from that vessel insures that the debris produced cannot flow upstream to enter into it. Instead the debris particles will be entrained within the infusate liquid and blood which is withdrawn through the aspiration line. The rate of blood withdrawn is preferably be kept to a minimum, e.g., 40 ml. per minute in the interests of patient safety.

In accordance with a preferred aspect of this invention the operation of the pumps 84 and 90 are coordinated so that $Q_2$ is equal to some variable times $Q_1$, where that variable is greater than 1 and is adjustable to accommodate the needs of the patient. Moreover, the coordination of the flow rates is preferably accomplished, automatically, so that a change in one flow rate automatically results in a proportional change in the other flow rate. This coordinated action may be accomplished by a mechanical linkage between the pumps, or by a common electrical controller for the pumps. Manual control of the pumps is also envisioned for some applications.

In any case, any suitable positive displacement pumps can be utilized, e.g., peristaltic pumps or piston pumps, in the system.

In order to expedite the revascularization of the bypass graft, the infusate liquid may be provided with a contrast medium, e.g., 30% contrast medium, so that the revascularization procedure can be viewed using conventional imaging techniques. Moreover, the infusate liquid can, if desired, be oxygenated to eliminate distal ischemia when the catheter is used for arterial restriction opening procedures. Also, if desired, small amounts of heparin, urokinase, etc., or other drugs can be added to the infusate liquid for the procedure.

Figure 5:
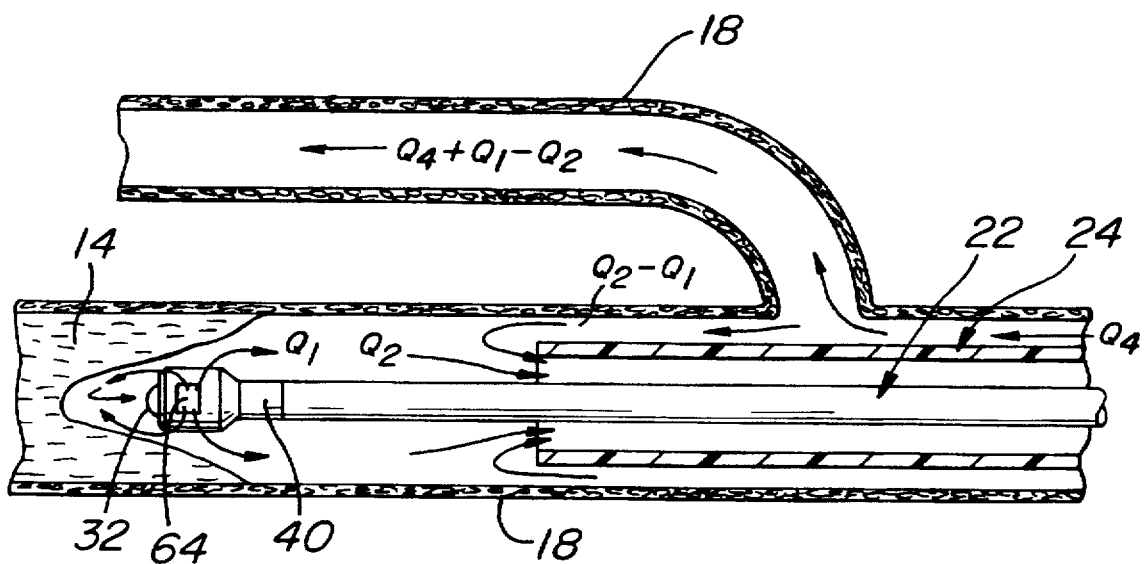
FIG. 5, is an illustration showing the apparatus of FIG. 1, partially in section, during the process of revascularizing a totally occluded femoral artery downstream of the profunda femoris.

As should be appreciated from the foregoing the subject invention provides a viable means for effecting the revascularization of partially or totally occluded coronary bypass grafts, while positively assuring that any debris particles produced during the revascularization procedure is removed from the patient's body. In addition, the subject invention is suitable for revascularizing other occluded vessels, as well. For example, in FIG. 5 the system is shown in use revascularizing a totally occluded femoral artery 18 downstream of the profunda femoris 18A. In this application the system functions to capture the debris created during the lumen opening procedure by preventing it from going along side the catheter and exiting down the profunda to end up in the distal capillary beds. In this application, a portion $Q_4+Q_1-Q_2$ of the blood flowing down the femoral artery 18 to the situs of the occlusion will be permitted to flow into the profunda femoris, while the portion $Q_2-Q_1$ of the blood and infusate liquid is diverted and/or withdrawn into the guide catheter to ensure positive debris removal in the same manner as described earlier. For some persons, e.g., diabetics with severely compromised distal capillary beds, a femoral artery revascularization procedure is likely to prove beneficial.

It must be reiterated that the atherectomy catheter for producing the lumen through the vascular occlusion need not be a rotary impacting device, like described above. Thus, a system 20 constructed in accordance with this invention may make use of any instrument having any type of working head, e.g., a reciprocating impacting working head, a combined rotary and reciprocating impacting working head, a rotary cutting head, a reciprocating cutting head, a rotary abrasive head, etc., to open the lumen in the occlusive material in the blood vessel. Moreover, the working head need not be shrouded. In fact, any of the heretofore identified prior art atherectomy devices can be utilized as part of the system 20. Some thrombectomy devices may also be utilized as part of the system 20. One such potential device is the Amplatz Thrombectomy Device designated by the trademark CLOT BUSTER by Microvena Corporation. It should also be pointed out that the working head of the device for forming the lumen need not even engage the occlusive material, so long as its lumen-opening operation produces debris particles to be removed. Thus, devices making use of liquid jets, laser beams, etc., can be utilized to open the lumen as part of the system of this invention. In short, any type of instrument for opening a lumen through the occlusive material and which produces debris can benefit from use in the system of this invention, i.e., a system which establishes a differential flow, wherein the infusate flow is less than the aspiration flow so that particles or pieces of occlusive material removed are positively precluded from flowing into adjacent vessels. Moreover, while the production of a local vortex flow adjacent the working head is desirable to effectuate the lumen opening process and to reduce debris particle size, it is not crucial to this invention.

Without further elaboration the foregoing will so fully illustrate our invention that others may, by applying current or future knowledge, adopt the same for use under various conditions of service.

What is claimed is:

1. An intravascular system for opening a lumen in an occluded blood vessel portion of a living being's vascular system, the occluded blood vessel portion being occluded by an occlusive material, said system comprising an instrument and debris extraction means, said instrument having an exterior surface and a working head and being arranged to be located within the being's vascular system, whereupon a passageway is established outside said exterior surface of said instrument and within the being's vascular system, said working head being arranged to operate on the occlusive material in the interior of the occluded blood vessel portion to open a lumen therein for the flow of blood therethrough, whereupon some debris may be produced from the occlusive material by the operation of said working head, said debris extraction means introducing an infusate liquid at a first flow rate adjacent said working head and withdrawing said liquid at a second and higher flow rate through said passageway to create a differential flow adjacent said working head, whereupon debris produced by the operation of said working head is withdrawn through said passageway by said differential flow for collection remote from the occluded vessel portion and is prevented from flowing into any upstream blood vessel or downstream blood vessel.

2. The intravascular system of claim 1 wherein the first and second flow rates are adjustable.

3. The intravascular system of claim 1 wherein said system establishes a vortex flow that circulates locally adjacent the working head.

4. The intravascular system of claim 3 wherein said working head comprises an impeller which establishes said vortex flow adjacent said working head.

5. The intravascular system of claim 4 wherein said impeller is a rotary member and wherein debris produced by the operation of said working head is in the form of particles which are carried by said vortex flow into repeated engagement with said impeller to reduce the size of such particles.

6. The intravascular system of claim 4 wherein said impeller is located within a shroud, said shroud having at least one opening through which said vortex flow passes.

7. The intravascular system of claim 1 wherein said working head is arranged to mechanically engage the occlusive material to open the lumen therein.

8. The intravascular system of claim 7 wherein said working head is an impacting member.

9. The intravascular system of claim 8 wherein said working head is a rotary member.

10. The intravascular system of claim 9 additionally comprising a flexible drive shaft coupled to said working head for effecting the rotation of said working head at a high rate of speed.

11. The intravascular system of claim 10 additionally comprising motor means for effecting the rotation of said flexible drive shaft.

12. The intravascular system of claim 1 wherein said instrument is arranged to introduce said infusate liquid at said first flow rate adjacent said working head.

13. The intravascular system of claim 12 wherein the first and second flow rates are adjustable.

14. The intravascular system of claim 12 wherein said instrument is arranged to be located within said catheter to form said passageway between said instrument and said catheter, said infusate liquid and the debris therein being withdrawn from the occluded blood vessel through said passageway.

15. The intravascular system of claim 14 wherein said debris extraction means comprises first pump means coupled to said instrument for establishing said first flow rate and second pump means coupled to said catheter for establishing said second flow rate.

16. The intravascular system of claim 12 wherein said system establishes a vortex flow that circulates locally adjacent the working head.

17. The intravascular system of claim 12 wherein said working head is a rotary member.

18. The intravascular system of claim 17 wherein said rotary member comprises an impeller which establishes a vortex flow that circulates locally adjacent the working head.

19. The intravascular system of claim 12 wherein said debris extraction means includes means for correlating said first and second flow rates to each other.

20. The intravascular system of claim 19 wherein said means for correlating enables said each of said first and second flow rates to be adjustable.

21. The intravascular system of claim 1 additionally comprising hydrodynamic steering means for steering said working head.

22. The intravascular system of claim 21 wherein said hydrodynamic steering means comprises a portion of said instrument and is located adjacent the working head, said instrument being arranged to be rotated about its central longitudinal axis to bring said hydrodynamic steering means to a desired orientation with respect to the central longitudinal axis of the blood vessel in which said instrument is located.

23. The intravascular system of claim 22 wherein said instrument has a distal end portion at which said working head is located and wherein said hydrodynamic steering means produces an unbalanced flow of fluid with respect to said instrument to propel said distal end portion of said instrument laterally of the central longitudinal axis of the blood vessel in which it is located.

24. The intravascular system of claim 23 wherein said instrument comprises a rotating working head located within a shroud, said shroud including at least one side directed window therein, said window forming at least one port of said hydrodynamic steering means.

25. The intravascular system of claim 24 wherein said rotary working head is arranged to impact the occlusive material to produce the lumen therethrough.

26. The intravascular system of claim 25 wherein said rotary working head is arranged to impact the occlusive material to produce the lumen therethrough.

27. The intravascular system of claim 26 wherein said instrument is arranged to be rotated about its central longitudinal axis to bring said window to a desired orientation with respect to the central longitudinal axis of the blood vessel in which said instrument is located.

28. The intravascular system of claim 25 wherein said instrument is arranged to be rotated about its central longitudinal axis to bring said window to a desired orientation with respect to the central longitudinal axis of the blood vessel in which said instrument is located.

29. The intravascular system of claim 21 wherein said instrument has a distal end portion at which said working head is located and wherein said hydrodynamic steering means produces an unbalanced flow of fluid with respect to said instrument to propel said distal end portion of said instrument laterally of the central longitudinal axis of the blood vessel in which it is located.

30. The intravascular system of claim 29 wherein said instrument comprises a rotating working head located within a shroud, said shroud including at least one side directed window therein, said window forming at least one port of said hydrodynamic steering means.

31. The apparatus of claim 1 wherein said system additionally comprises a tubular member arranged for introduction into the being's vascular system adjacent the occluded blood vessel portion, said instrument being arranged to be disposed within said tubular member to establish said passageway between said tubular member and said instrument.

32. The apparatus of claim 31 wherein said tubular member is arranged to introduce and guide said working head of said instrument to a position adjacent the occlusive material.

33. An intravascular system for opening a lumen in an occluded blood vessel portion of a living being's vascular system, said occluded blood vessel portion being occluded by an occlusive material, said system comprising an instrument, a catheter and debris extraction means, said instrument including a working head, said instrument being located within said catheter, said working head being arranged to operate on the occlusive material in the interior of the occluded blood vessel portion to open a lumen therein for the flow of blood therethrough, whereupon some debris may be produced from the occlusive material by the operation of said working head, said debris extraction means including debris removal means coupled to said catheter, said debris extraction means being arranged for introducing an infusate liquid through said instrument at a first flow rate to a position adjacent said working head, said debris extraction being also being arranged for withdrawing said liquid at a second and higher flow rate to create a differential flow adjacent said working head, whereupon debris produced by the operation of said working head is withdrawn by said differential flow for collection remote from the occluded vessel portion and is prevented from flowing into any upstream blood vessel or downstream blood vessel, said infusate liquid and the debris therein being withdrawn from the occluded blood vessel portion through said passageway under the influence of said debris removal means.

34. The intravascular system of claim 33 wherein said catheter comprises a guide catheter.

35. The intravascular system of claim 33 wherein said catheter comprises an introducer sheath.

36. The intravascular system of claim 33 wherein the first and second flow rates are correlated to each other.

37. The intravascular system of claim 36 wherein said first and second flow rates are adjustable.

38. The intravascular system of claim 33 wherein said debris extraction means comprises first pump means coupled to said instrument for establishing said first flow rate and wherein said debris removal means comprises second pump means for establishing said second flow rate.

39. The intravascular system of claim 38 wherein said first and second pump means are each positive displacement pumps.

40. The intravascular system of claim 33 wherein said instrument and said catheter are each sufficiently flexible to be passed longitudinally through a portion of the vascular system so that said working head is located adjacent the occluded blood vessel portion.

41. A method for opening a lumen in an occluded blood vessel portion of a living being's vascular system located downstream of a first blood vessel portion from which blood will flow to the occluded blood vessel portion, the occluded blood vessel portion being occluded by an occlusive material and being located upstream of a second blood vessel portion, said method comprising:

(a) providing a working head and debris extraction means within the being's vascular system, (b) operating said working head on the occlusive material in the interior of the occluded blood vessel portion to open a lumen for the flow of blood therethrough to said second blood vessel portion, whereupon some debris may be produced from the occlusive material by the operation of said working head, (c) causing said debris extraction means to introduce an infusate liquid at a first flow rate adjacent said working head, and (d) causing said debris extraction means to withdraw said liquid at a second and higher flow rate to create a differential flow adjacent said working head, whereupon debris produced by the operation of said working head is withdrawn for collection remote from the occluded blood vessel portion.

42. The method of claim 41 wherein said differential flow prevents debris produced by the operation of said working head from flowing into either the first blood vessel portion or the second blood vessel portion.

43. The method of claim 42 wherein said occluded blood vessel portion comprises a bypass graft.

44. The method of claim 43 wherein the bypass graft is a coronary bypass graft, wherein said living being's vascular system includes an aorta, and wherein the first vessel portion comprises the aorta.

45. The method of claim 43 wherein said living being's vascular system includes a femoral artery and wherein the occluded blood vessel portion comprises a portion of the femoral artery.

46. The method of claim 45 wherein said living being's vascular system includes a profunda femoris and wherein the first blood vessel portion comprises the profunda femoris.

47. The method of claim 41 additionally comprising:

(d) establishing a vortex flow that circulates locally adjacent said working head.

48. The method of claim 41 wherein said working head is arranged to engage the occlusive material to open the lumen therein.

49. The method of claim 48 wherein said working head is a rotary member which is rotated to cause to repeatedly engage the occlusive material to open the lumen therein.

50. The method of claim 49 wherein the repeated engagement causes portions of the occlusive material to be removed to produce the lumen therethrough.

51. The method of claim 49 wherein said repeated engagement comprises repeated impacting of the occlusive material, to break portions of the occlusive material away to produce the lumen.

52. The method of claim 50 additionally comprising:

(d) establishing a vortex flow that circulates locally adjacent said working head.

53. The method of claim 50 wherein said vortex flow carries removed portion of the occlusive material into repeated engagement with said working.

* * * * *